United States Patent [19]
Nakada et al.

[11] Patent Number: 5,800,411
[45] Date of Patent: Sep. 1, 1998

[54] CATHETER

[75] Inventors: Mamoru Nakada; Minoru Shinozuka, both of Hachioji, Japan

[73] Assignee: Olympus Optical Co., Ltd., Tokyo, Japan

[21] Appl. No.: 709,065

[22] Filed: Sep. 6, 1996

[30] Foreign Application Priority Data

Oct. 6, 1995 [JP] Japan ................................. 7-259991

[51] Int. Cl.⁶ .................................................. A61M 29/00
[52] U.S. Cl. ............................................ 604/280; 604/96
[58] Field of Search .................. 604/53, 164, 280–284; 606/191, 194

[56] References Cited

U.S. PATENT DOCUMENTS 5,066,278  11/1991  Hirschberg et al. .
5,593,412  1/1997  Martinez et al. .................... 604/96

FOREIGN PATENT DOCUMENTS

| A-208787 | 1/1987 | European Pat. Off. . |
| A-547463 | 6/1993 | European Pat. Off. . |
| A-2707505 | 1/1995 | France . |
| U-8710340 | 10/1987 | Germany . |

*Primary Examiner*—Michael Buiz
*Assistant Examiner*—William Lewis
*Attorney, Agent, or Firm*—Kenyon & Kenyon

[57] ABSTRACT

A catheter to be used as an injection tube includes a flexible sheath to be inserted into a celom through an insertion channel of an endoscope for injecting a medicinal solution or the like into the celom through the sheath. The sheath includes a distal end portion which has a distal aperture smaller than the inside diameter of the sheath, a frontmost portion rounded with a radius of curvature larger than the thickness of the wall of the sheath, and at least one slit extending to the distal aperture.

34 Claims, 6 Drawing Sheets

CATHETER

BACKGROUND OF THE INVENTION

1. Field of the Invention

The present invention relates to a catheter to be inserted into an insertion channel of an endoscope for injecting a contrast medium or the like.

2. Description of the Related Art

In pancreatography or cholangiography, a contrast medium injection tube is inserted into a celom through an insertion channel of a duodenal endoscope, and the distal end of the injection tube is inserted into the pancreatic duct or the bile duct through the duodenal papilla to inject a contrast medium. Such a contrast medium injection tube is disclosed in, for example, Japanese Laid-Open Utility Model Application Publication No. Sho 57-113152.

Generally, the distal end portion of the injection tube is tapered for easy insertion into the duodenal papilla.

Figure 6:
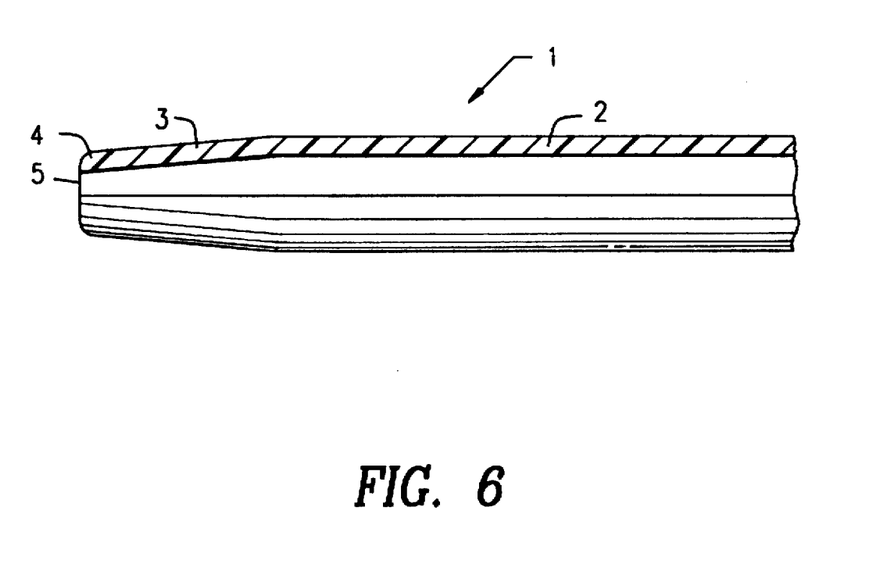
FIG. 6 is a longitudinal sectional view of a distal end portion of a conventional tube for injecting a contrast medium.

FIG. 6 shows a common structure of a contrast medium injection tube.

A contrast medium injection tube 1 comprises an insertion tube 2 and a distal end portion 3 which is tapered so that it can be easily inserted into a celom. The front edge of the distal end portion 3 is formed as a round chamfer 4 since if the edge is sharp, it will injure the tissue in the celom. An aperture 5 for spouting the contrast medium is formed at the distal end of the tube 1.

If the pancreatic duct or the bile duct has a strictured portion, a guide wire is inserted into the strictured portion and followed by the injection tube so that the injection tube can pass through the strictured portion. For this purpose, it is necessary to insert the guide wire into the aperture 5. Therefore, the diameter of the aperture 5 is required to be larger than that of the guide wire As a result, the distal end portion 3 of the injection tube 1 cannot be largely tapered for easy insertion. Further, the round chamfer 4 formed at the front edge of the distal end portion 3 cannot be rounded with a large radius of curvature. As a result, when the distal end portion 3 is inserted into a thin duct such as the pancreatic duct, the bile duct or the like, for example, from the duodenal papilla, the distal end 3 portion cannot easily be inserted into the duct. Moreover, the distal end portion 3 may hurt the inside wall of the duct or its peripheral tissues.

Japanese Laid-Open Utility Model Application Publication No. Hei 3-13157 discloses a catheter comprising a closed distal end portion, which is provided with a slit as a valve for preventing counterflow of body fluid. When fluid having a high viscosity such as a cholangiographic agent is injected through such a catheter, it is difficult to spout the fluid from the closed distal end portion. In the catheter, the thickness of the wall of the distal end portion is designed to be thick to close the distal end portion, and the slit provided in the distal end portion is designed to be small. As a result, considerable force may be required to insert the guide wire in the catheter. Thus, the guide wire is not easy to operate and may be buckled.

SUMMARY OF THE INVENTION

It is an object of the present invention to provide a catheter whose distal end portion has a small outside diameter and can be rounded with a large radius of curvature without degrading the function of easily spouting a contrast medium forward so that the catheter can be easily inserted into a thin duct such as the bile duct and a guide wire can be easily inserted in the catheter.

A catheter of the present invention comprises a flexible sheath inserted into a celom through an insertion channel.

A catheter of the present invention comprises a flexible sheath to be inserted into a celom through an insertion channel of an endoscope for injecting fluid such as a medicinal solution into the celom through the flexible sheath, wherein the sheath has an inside diameter and a wall having a thickness and comprises a distal end portion which has a distal aperture having a diameter smaller than the inside diameter of the flexible sheath, a frontmost part rounded with a radius of curvature larger than the thickness of the wall of the sheath, and at least one slit extending to the aperture.

Other features and many of the attendant advantages of this invention will appear in the course of the description thereof which follows.

DESCRIPTION OF THE PREFERRED EMBODIMENTS

Figure 1A:
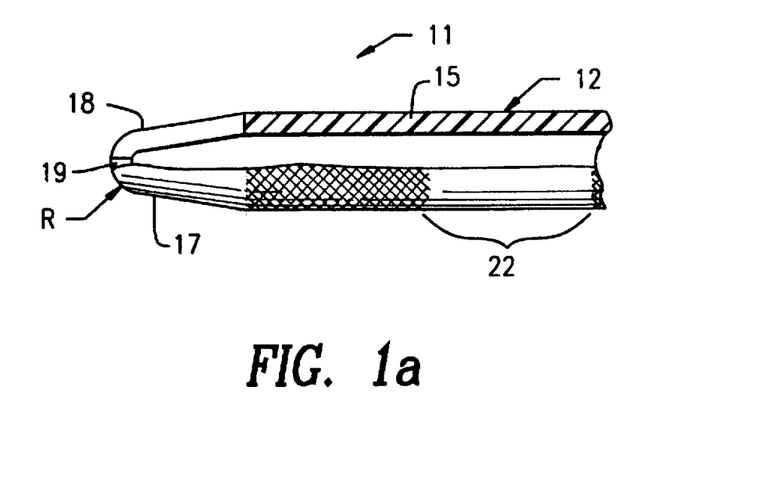
FIG. 1(a) is a longitudinal partially sectional view of a distal end portion of a contrast medium injection tube of a first embodiment of the present invention.
Figure 1B:
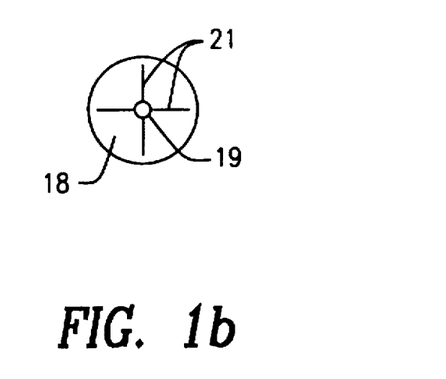
FIG. 1(b) is a front view of a distal end portion of the injection tube of the first embodiment of the present invention.
Figure 2:
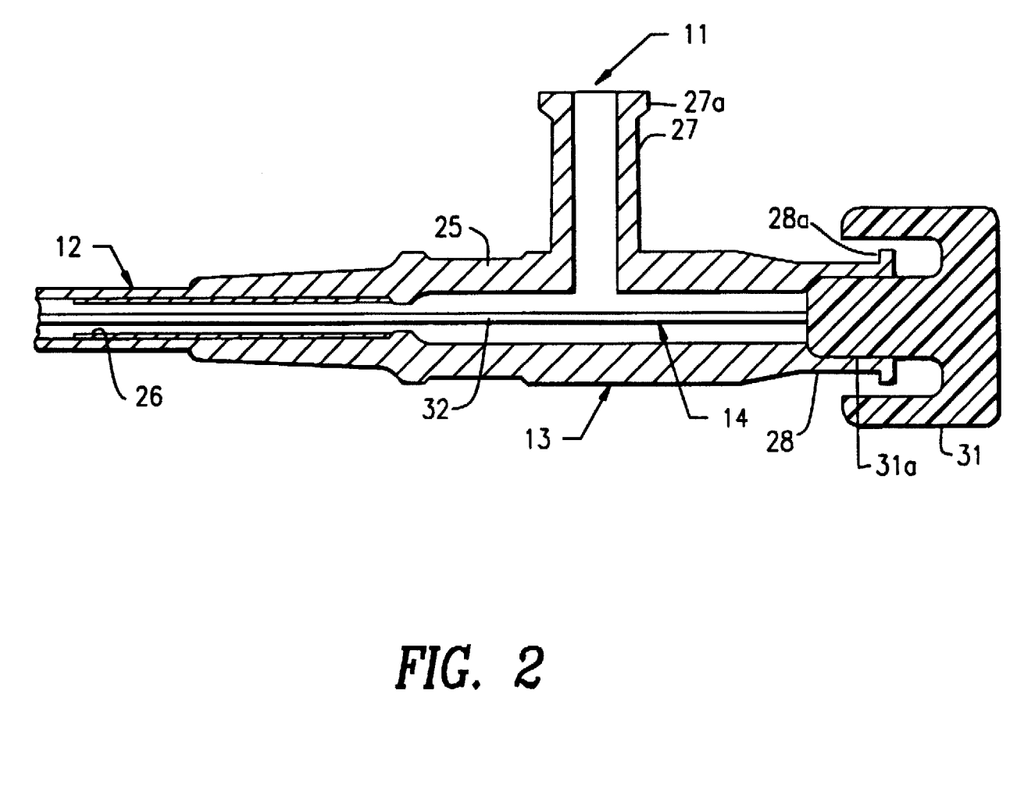
FIG. 2 is a longitudinal sectional view of a proximal operating portion of the injection tube of the first embodiment of the present invention.
Figure 3:
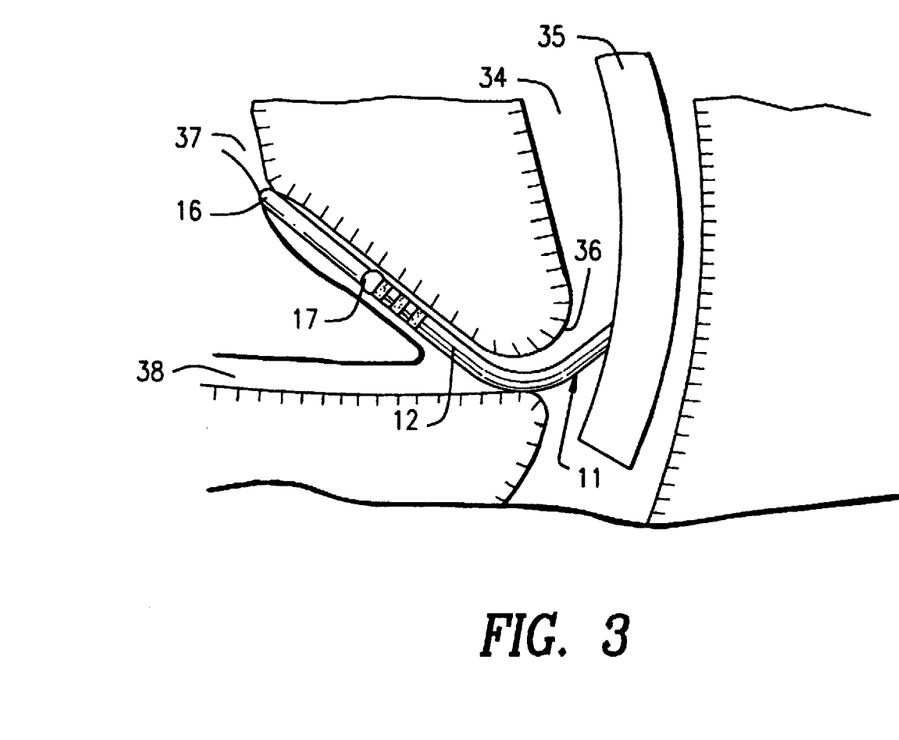
FIG. 3 is an illustration for explaining the operation of the injection tube of the first embodiment of the present invention as it is inserted into a bile duct through a duodenum.

FIGS. 1–3 show a first embodiment of the present invention.

The catheter of this first embodiment is a contrast medium injection tube 11 for pancreatography, cholangiography or the like. Different portions of the injection tube 11 are illustrated by FIGS. 1(a) and 2. The injection tube 11 comprises an insertion tube 12, which is illustrated in FIG. 1(a), and a proximal operating portion, which is illustrated in FIG. 2. The insertion tube 12 is inserted into an insertion channel of a duodenal endoscope for the duodenum, and the proximal operating portion 13 is operated by an operator for fluid feeding or the like. In addition, a stylet 14 is provided for preventing the insertion tube 12 from buckling. A front end portion of a tube for injecting a contrast medium is shown in FIG. 1(a). FIG. 1(a) is a partially sectional view of a distal end portion 17 of the contrast medium injection tube as a catheter, and FIG. 1(b) is a front view of the distal end portion 17. The insertion tube 12 of the injection tube 11 is formed by a flexible sheath 15, which can be inserted into the pancreatic duct or the bile duct through the insertion channel of the duodenal endoscope for injecting a contrast medium into the pancreatic duct or the bile duct. The inside and outside diameters and material of the flexible sheath 15 are so selected that a guide wire 16 (See FIG. 3) as well as the stylet 14 can be inserted therein. Specifically, the outside diameter is 1.5 mm to 2.5 mm and the inside diameter is 0.7 mm to 1.7 mm. The material is a thermoplastic resin, such as a fluorinated polymer, for example, polytetrafluoroethylene (PTFE) or fluorinated ethylene propylene (FEP), which has a small coefficient of surface friction and is flexible and cannot be easily crushed so that the flexible sheath 15 can pass a forceps raising member of the duodenal endoscope without buckling.

A distal end portion 17 of the flexible sheath 15 is tapered by thermoforming for easy insertion into the duodenal papilla. A frontmost part 18 of the distal end portion 17 is rounded with a radius of curvature R in order not to injure the tissue in the celom. Considering the size of a distal aperture 19 which will be described below, the radius of curvature R of the frontmost part 18 is set, for example, to approximately satisfy the following equation:

$$R=(D-d)/2$$

where D is the outside diameter of the flexible sheath 15, and d is the diameter of the aperture 19. The frontmost part 18 of the flexible sheath 15 is provided at its center with the distal aperture 19 having a diameter of 0.1 mm to half of the inside diameter of the flexible sheath 15 so that the contrast medium introduced through the flexible sheath 15 can be easily spouted forward and the distal end portion 17 can be thin. As shown in FIG. 1(b), slits 21 perpendicular to each other are provided in a wall of the distal end portion 17, especially of the frontmost part 18. The slits 21 are normally closed, and when a guide wire 16 (See FIG. 3) is about to protrude through them, the slits 21 are opened and the distal end portion 17, especially the frontmost part 18 is expanded outward, thereby allowing the insertion of the guide wire 16 having a diameter larger than that of the aperture 19. The number of the slits 21 is preferably four or more so that the guide wire 16 can easily come out through the frontmost part 18 by a little force. The slits 21 are cut from the frontmost part 18 of the flexible sheath 15 to the tapered periphery of the distal end portion 17. The thickness of the wall of the distal end portion 17 including the slits 21 is smaller than that of the flexible sheath 15. Black markings 22 are provided at regular intervals on the outer surface of the distal end portion 17 of the flexible sheath 15 so that when the flexible sheath 15 is inserted into the duodenal papilla, its insertion length can be confirmed under the endoscopic observation. Further, a chip or the like which does not transmit X-rays may be provided since the contrast medium is often injected into the pancreatic duct or the bile duct via an endoscope under fluoroscopy.

FIG. 2 is a longitudinal sectional view of a proximal operating portion of the contrast medium injection tube 11. The operating portion 13 comprises a main body 25 which is cylindrical as a whole and coaxial with the insertion tube 12. The shape of the main body 25 is cylindrical. The proximal end of the insertion tube 12 is coupled with the front end portion of the main body 25 via a pipe 26. The pipe 26 is inserted into and bonded to both the proximal end of the insertion tube 12 and the front end portion of the main body 25. An injection cock 27 is located in the middle of the main body 25. The injection cock 27 is provided with a Luer lock 27a to which a syringe barrel for liquid or water feeding may be attached. The main body 25 is provided at its rear end portion with another cock 28, which is also provided with a Luer lock 28a. The syringe or the like may be attached to the ring 28a of the cock 28, but a Luer taper portion 31a of a knob 31 of the stylet 14 inserted into the tube 11 is normally fitted to the Luer lock 28a. The stylet 14 comprises a wire 32, fixedly coupled with the knob 31 by gluing or welding, for preventing the tube 12 from buckling.

Referring to FIG. 3, operations of the tube 11 will be described. First, the insertion tube 12 of the injection tube 11 is inserted into the insertion channel of an endoscope 35 inserted into the duodenum 34, and the distal end portion 17 of the injection tube 11 is protruded from the distal end portion of the endoscope 35. Then, the distal end portion 17 of the injection tube 11 is inserted into the bile duct 37 or the pancreatic duct 38 through the duodenal papilla 36 by bending the endoscope 35, raising the treating instrument raising member, or the like operation. Further, a syringe barrel is attached to the Luer lock 27a of the injection cock 27, and the contrast medium is fed through the hollow interior of the flexible sheath 15 and the aperture 19 into the bile duct 37 or the pancreatic duct 38. After the shape of the bile duct 37 or the pancreatic duct 38, the existence or nonexistence of a calculus, or the like is confirmed under fluoroscopy, the injection tube 11 is removed from the insertion channel of the endoscope 35. In addition to the aperture 19, a plurality of holes as side holes for spouting the contrast medium may be provided.

The guide wire 16 may be used when it is necessary. For example, when there is a strictured portion in the bile duct 37 or the pancreatic duct 38 so that the injection tube 11 cannot be advanced further, the stylet 14 is removed from the injection tube 11, and the guide wire 16 is inserted from the Luer lock 28a of the cock 28. Then, the guide wire 16 is inserted through the hollow interior of the tube 11 and advanced until it passes the strictured portion of the bile duct 37 or the pancreatic duct 38. After confirming that the guide wire 16 has passed the strictured portion, the injection tube 11 is advanced along the guide wire 16 to pass the strictured portion. After the contrast medium has been injected, the guide wire 16 may be left alone with the injection tube 11 only being removed in order to facilitate further treatment of the pancreatic duct 38 or the bile duct 37. For example, an incision instrument or the like for duodenotomy can be easily inserted along the remaining guide wire 16 into the bile duct 37 through the duodenal papilla 36.

In order to insert the injection tube 11 into a thin duct such as the bile duct 37 or the pancreatic duct 38 from the duodenal papilla 36, the distal end portion 17 of the insertion tube 12 is required to be thin. Moreover, in order not to damage the inside wall of celom and its peripheral tissues, the frontmost part 18 is required to be rounded with a radius of curvature as large as possible.

According to the first embodiment of the present invention, the injection tube 11 has the aperture 19 smaller than the inside diameter of the tube 11, and at least one slit 21 extending to the aperture 19 so that the distal end portion 17 can be rounded thereby facilitating the insertion into the thin duct such as the bile duct 37 without damaging the body tissue. Further, since the distal end portion 17 of the flexible sheath 15 can be expanded outward owing to the slits 21, the guide wire 16 having a diameter larger than that of the aperture 19 can be inserted. Moreover, when the contrast medium is injected, the contrast medium can be spouted forward through the slits 21 in addition to the aperture 19 so that the liquid injecting operation can be easily implemented, even though the diameter of the aperture 19 is designed to be smaller than that of the conventional tube for contrast medium injection. It is not necessary that the number of the slits 21 is four. Even one slit is provided, the same advantages can be obtained.

Figure 4A:
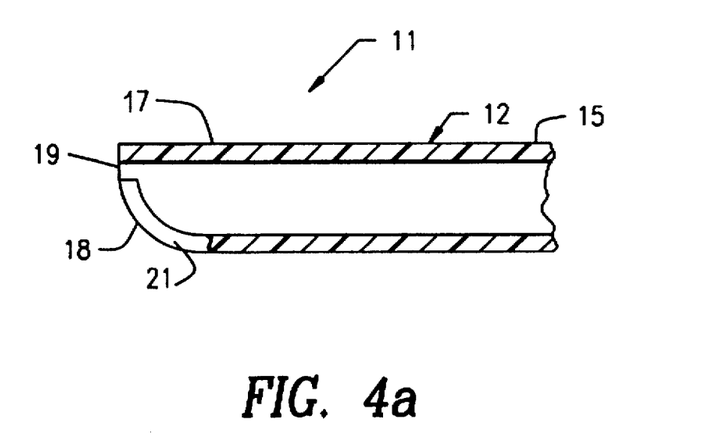
FIG. 4(a) is a longitudinal sectional view of a distal end portion of a contrast medium injection tube of a second embodiment of the present invention.
Figure 4B:
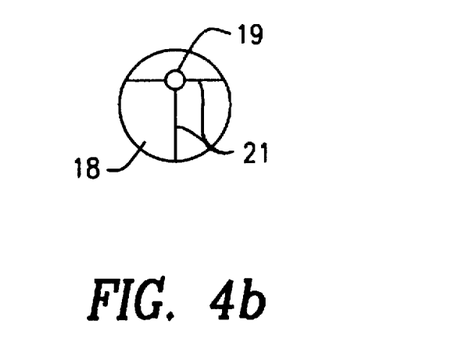
FIG. 4(b) is a front view of a distal end portion of the injection tube of the second embodiment of the present invention.

Referring to FIGS. 4(a) and 4(b), a second embodiment of the present invention will now be described.

FIG. 4 (a) is a longitudinal sectional view of a distal end portion 17 of a contrast medium injection tube as a catheter, and FIG. 4(b) is a front view of the second embodiments of the present invention.

The catheter of this embodiment is also a contrast medium injection tube 11 for pancreatography, cholangiography or the like. A distal end portion 17 of an insertion tube 12 is provided with an aperture 19 which is eccentric to the central axis of a flexible sheath 15. The distal end portion 17 is provided with three slits 21. As shown in FIG. 4(a), a curved surface of a frontmost part 18 extends from the outer surface of the insertion tube 12 to the eccentric aperture 19 and is rounded in a substantially semi-spherical form extending to the wall of the insertion tube 12. The center of the curve of the frontmost part 18 is positioned on the side of the aperture 19, for example, approximately on the inner surface of the insertion tube 12. As shown in FIG. 4(b), two of the three slits 21 start from the aperture 19 and are arranged left and right in a horizontal straight line, and the other one slit 21 is perpendicular thereto. The structures of the other elements are the same as those of the first embodiment of the present invention. The catheter of the second embodiment is used in the same way as that used in the first embodiment.

According to the second embodiment, in addition to the effects of the catheter of the first embodiment, the possibility for injuring the tissue in a celom during insertion can be further reduced since the distal end portion 17 of the flexible sheath 15 can be rounded with a larger radius of curvature.

Figure 5:
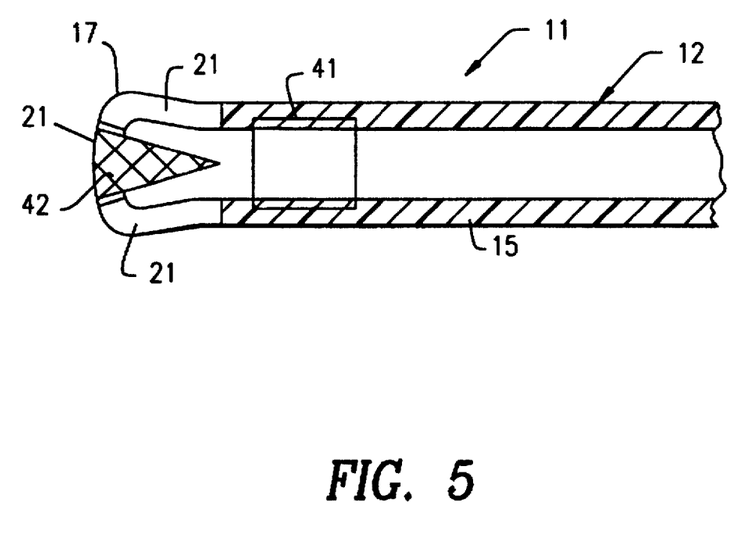
FIG. 5 is a longitudinal sectional view of a distal end portion of a contrast medium injection tube of a third embodiment of the present invention.

Referring to FIG. 5, a third embodiment of the present invention will now be described.

FIG. 5 is a longitudinal sectional view of a distal end portion of a contrast medium injection tube.

The catheter of this embodiment is also a contrast medium injection tube 11 for pancreatography, cholangiography or the like. A pipe 41 made of an X-ray untransmissive material such as stainless steel, platinum, tungsten or the like is forced into the vicinity of the distal end portion 17 of a flexible sheath 15 of the catheter. The distal end portion 17 of the flexible sheath 15 is provided with, for example, four slits 21 in the same way as in the first embodiment. The outer surface of the distal end portion 17 is covered by a film 42 which is made of an elastic thermoplastic resin such as polyurethane, silicone or the like and has an opening whose shape is substantially the same as that of the aperture 19 (of FIG. 1(b)), the opening being aligned with the aperture 19. When the slit 21 is cracked, the film 42 expands over the outside of the crack so that no gap is formed in the outer surface of the distal end portion. The structures of the other elements are the same as those of the first embodiment of the present invention. The catheter of the third embodiment is used in the same way as that of in the first embodiment.

According to the third embodiment, in addition to the effects of the first embodiment, the position of the distal end portion 17 of the injection tube 11 can be confirmed during the treatment under fluoroscopy since the pipe 41 made of an x-ray untransmissive material is embedded in the distal end portion 17. Further, since the film 42 covers the slits 21, even if the slit is cracked, no body tissue will enter the slit 21 so that no mucus membrane will be caught and injured.

This invention can be applied not only to the contrast medium injection tube but also to balloon catheters, incision instruments, and all other endoscopic treating instruments using a guide wire.

While only certain preferred features of the invention have been shown by way of illustration, many modifications and changes will occur to those skilled in the art. It is, therefore, to be understood that the appended claims are intended to cover all such modifications and changes which fall within the true spirit of the invention.

What is claimed is:

1. A catheter comprising a flexible sheath to be inserted into a celom through an insertion channel of an endoscope for injecting liquid such as a medicinal solution into the celom through the flexible sheath, wherein the flexible sheath has an inside diameter and a wall having a thickness and comprises a distal end portion which has a distal aperture having a diameter smaller than the inside diameter of the flexible sheath, a frontmost part of the distal end portion being rounded with a radius of curvature larger than the thickness of the wall of the flexible sheath, and at least one slit extending to the aperture, wherein the at least one slit is covered by an elastic film.

2. The catheter of claim 1, wherein the aperture has a diameter of at least 0.1 mm and at most half of the inside diameter of the flexible sheath.

3. The catheter of claim 1, wherein the distal end portion has a wall whose thickness is not more than the thickness of the wall of the flexible sheath.

4. The catheter of claim 1, wherein the at least one slit extends from the aperture to the wall of the flexible sheath.

5. The catheter of claim 1, wherein the flexible sheath has an outside diameter D, the aperture has a diameter d, and the radius of curvature of the frontmost part of the distal end portion is substantially equal to (D−d)/2.

6. The catheter of claim 1, wherein the flexible sheath has an outside diameter of 1.5 mm to 2.5 mm.

7. The catheter of claim 1, wherein the inside diameter of the flexible sheath is 0.7 mm to 1.7 mm.

8. The catheter of claim 1, wherein the flexible sheath is made of a thermoplastic resin.

9. The catheter of claim 8, wherein the thermoplastic resin is selected from the group consisting of polytetrafluorethylene (PTFE) and fluorinated ethylene propylene (FEP).

10. The catheter of claim 1, wherein the number of the slits is at least four.

11. The catheter of claim 1, wherein the distal end portion of the flexible sheath has an outer surface on which a marker is provided.

12. The catheter of claim 1, wherein the flexible sheath has a central axis and the aperture is eccentric to the central axis.

13. The catheter of claim 12, wherein the flexible sheath has an outer surface and an outside diameter and the frontmost part of the flexible sheath extends from the outer surface to the eccentric aperture and rounded with a radius of curvature substantially equal to half of the outside diameter of the flexible sheath.

14. The catheter of claim 1, wherein the distal end portion of the flexible sheath has an outer surface on which an X-ray untransmissive member is provided.

15. The catheter of claim 14, wherein the X-ray untransmissive member is made of a material selected from the group consisting of stainless steel, platinum and tungsten.

16. The catheter of claim 1, wherein the film is made of a thermoplastic resin.

17. The catheter of claim 16, wherein the thermoplastic resin is selected from the group consisting of polyurethane and silicone.

18. A catheter comprising a flexible sheath to be inserted into a pancreatic duct or a bile duct through an insertion channel of a duodenal endoscope for injecting a contrast medium into the pancreatic duct or the bile duct through the flexible sheath, wherein the flexible sheath has an inside diameter and a wall having a thickness and comprises a distal end portion which has a distal aperture having a diameter smaller than the inside diameter of the flexible sheath, a frontmost part of the distal end portion being rounded with a radius of curvature larger than the thickness of the wall of the flexible sheath, and at least one slit extending to the aperture, wherein the at least one slit is covered by an elastic film.

19. The catheter of claim 18, wherein the aperture has a diameter of at least 0.1 mm and at most half of the inside diameter of the flexible sheath.

20. The catheter of claim 18, wherein the distal end portion has a wall whose thickness is not more than the thickness of the wall of the flexible sheath.

21. The catheter of claim 18, wherein the at least one slit extends from the aperture to the wall of the flexible sheath.

22. The catheter of claim 18, wherein the flexible sheath has an outside diameter D, the aperture has a diameter d, and the radius of curvature of the frontmost part of the distal end portion is substantially equal to (D–d)/2.

23. The catheter of claim 18, wherein the flexible sheath has an outside diameter of 1.5 mm to 2.5 mm.

24. The catheter of claim 18, wherein the inside diameter of the flexible sheath is 0.7 mm to 1.7 mm.

25. The catheter of claim 18, wherein the flexible sheath is made of a thermoplastic resin.

26. The catheter of claim 25, wherein the thermoplastic resin is selected from the group consisting of polytetrafluorethylene (PTFE) and fluorinated ethylene propylene (FEP).

27. The catheter of claim 18, wherein the number of the slits is at least four.

28. The catheter of claim 18, wherein the distal, end portion of the flexible sheath has an outer surface on which a marker is provided.

29. The catheter of claim 18, wherein the flexible sheath has a central axis and the aperture is eccentric to the central axis.

30. The catheter of claim 29, wherein the flexible sheath has an outer surface and an outside diameter and the frontmost part of the flexible sheath extends from the outer surface to the eccentric aperture and rounded with a radius of curvature substantially equal to half of the outside diameter of the flexible sheath.

31. The catheter of claim 18, wherein the distal end portion of the flexible sheath has an outer surface on which an X-ray untransmissive member is provided.

32. The catheter of claim 31, wherein the X-ray untransmissive member is made of a material selected from the group consisting of stainless steel, platinum and tungsten.

33. The catheter of claim 18, wherein the film is made of a thermoplastic resin.

34. The catheter of claim 33, wherein the thermoplastic resin is selected from the group consisting of polyurethane and silicone.

* * * * *